(12) United States Patent
Zenoni et al.

(10) Patent No.: US 9,096,491 B2
(45) Date of Patent: Aug. 4, 2015

(54) PRODRUG OF AN ANTI-INFLAMMATORY ACTIVE INGREDIENT

(75) Inventors: Maurizio Zenoni, Patrica (IT);
Umberto Ciambecchini, Patrica (IT);
Lorenzo De Ferra, Patrica (IT); Stefano Turchetta, Patrica (IT); Vincenzo De Sio, Patrica (IT)

(73) Assignee: CHEMI S.P.A., Cinisello Balsamo (IT)

( * ) Notice: Subject to any disclaimer, the term of this patent is extended or adjusted under 35 U.S.C. 154(b) by 0 days.

(21) Appl. No.: 14/232,020

(22) PCT Filed: Jul. 9, 2012

(86) PCT No.: PCT/EP2012/063414
§ 371 (c)(1),
(2), (4) Date: Feb. 14, 2014

(87) PCT Pub. No.: WO2013/007694
PCT Pub. Date: Jan. 17, 2013

(65) Prior Publication Data
US 2014/0163251 A1    Jun. 12, 2014

(30) Foreign Application Priority Data

Jul. 11, 2011   (IT) .............................. MI2011A1288

(51) Int. Cl.
C07C 227/04  (2006.01)
C07C 229/64  (2006.01)
C07C 229/42  (2006.01)

(52) U.S. Cl.
CPC ............. *C07C 227/04* (2013.01); *C07C 229/42* (2013.01); *C07C 229/64* (2013.01)

(58) Field of Classification Search
None
See application file for complete search history.

(56) References Cited

U.S. PATENT DOCUMENTS

2013/0079399 A1*   3/2013   Labruzzo ...................... 514/485

FOREIGN PATENT DOCUMENTS

| WO | 2004000786 | 12/2003 |
| WO | 2011148297 | * 12/2011 |

OTHER PUBLICATIONS

International Search Report issued in counterpart PCT Application No. PCT/EP2012/063414, Sep. 11, 2012.
Written Opinion of International Searching Authority issued in counterpart PCT Application No. PCT/EP2012/063414, Sep. 11, 2012.

* cited by examiner

*Primary Examiner* — Karl J Puttlitz
(74) *Attorney, Agent, or Firm* — Silvia Salvadori, P.C.

(57) ABSTRACT

A process for the preparation of a prodrug of 5-aminosalicylic acid, namely 2-butanoyloxy-5-amino-benzoic acid, and solid forms of such compound are described.

1 Claim, 14 Drawing Sheets

FIGURE 1 – PXRD of form I
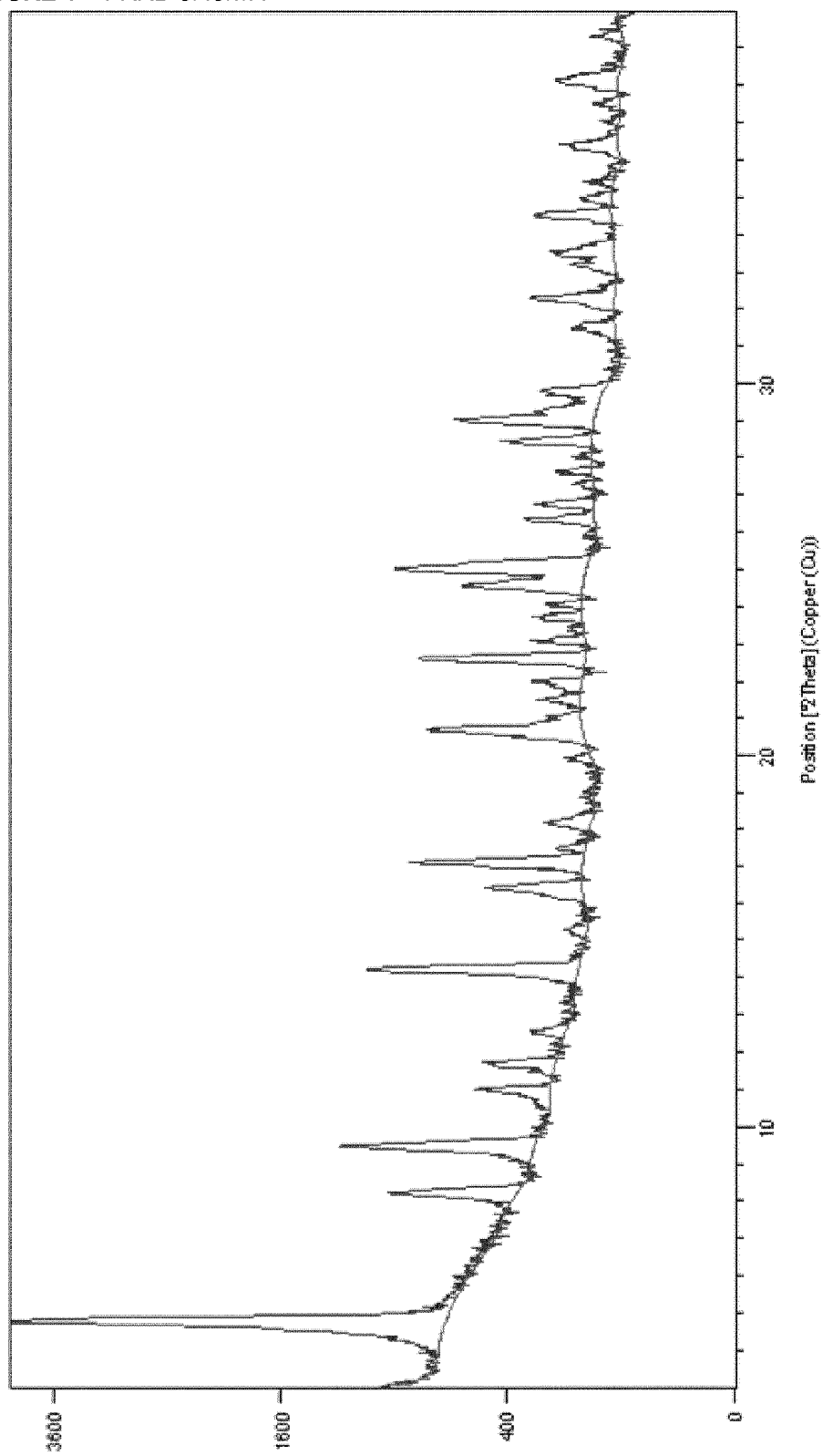

FIGURE 2 – FTIR of form I
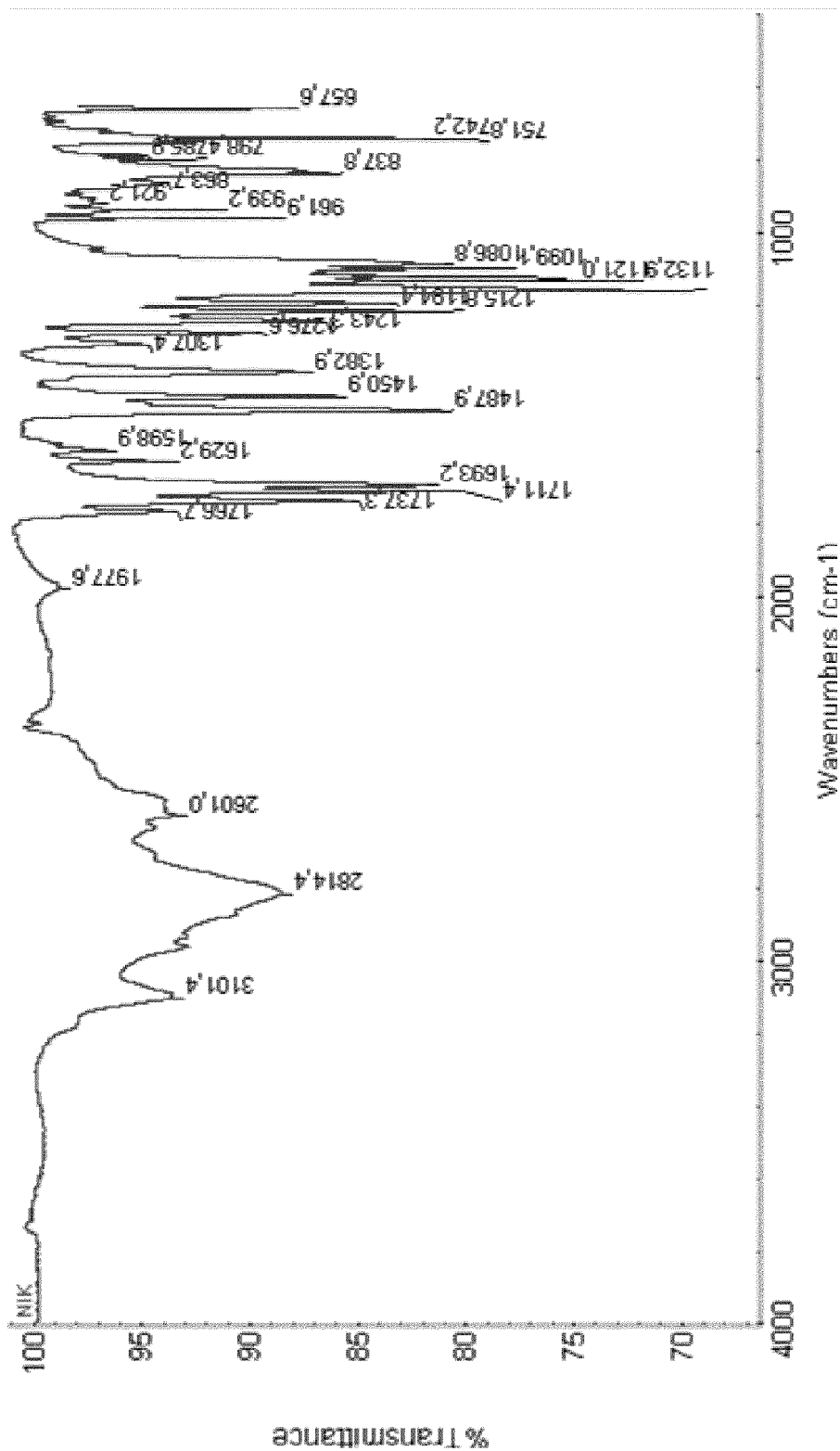

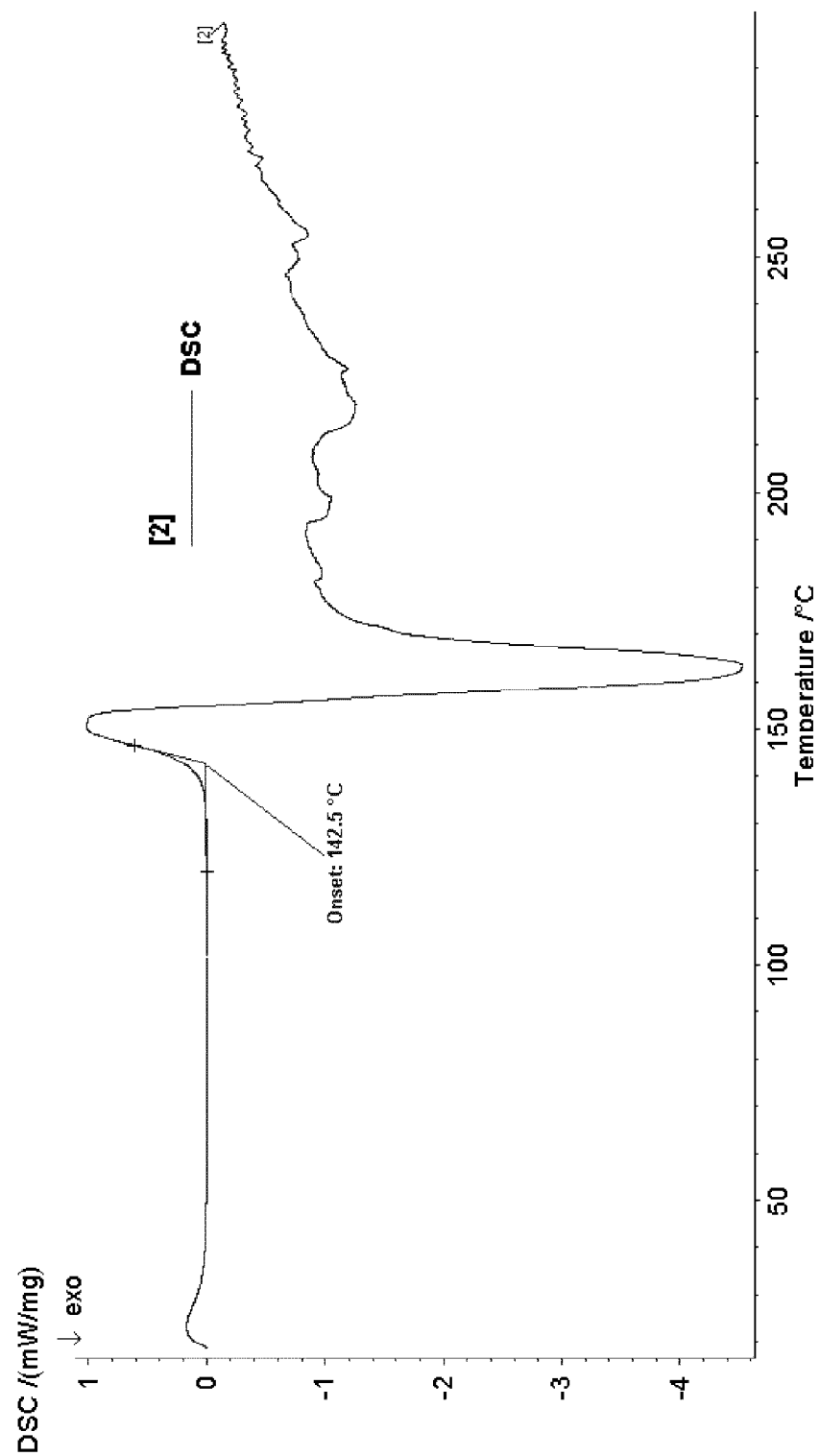
FIGURE 3 – DSC of form I

FIGURE 4 – TGA of form I
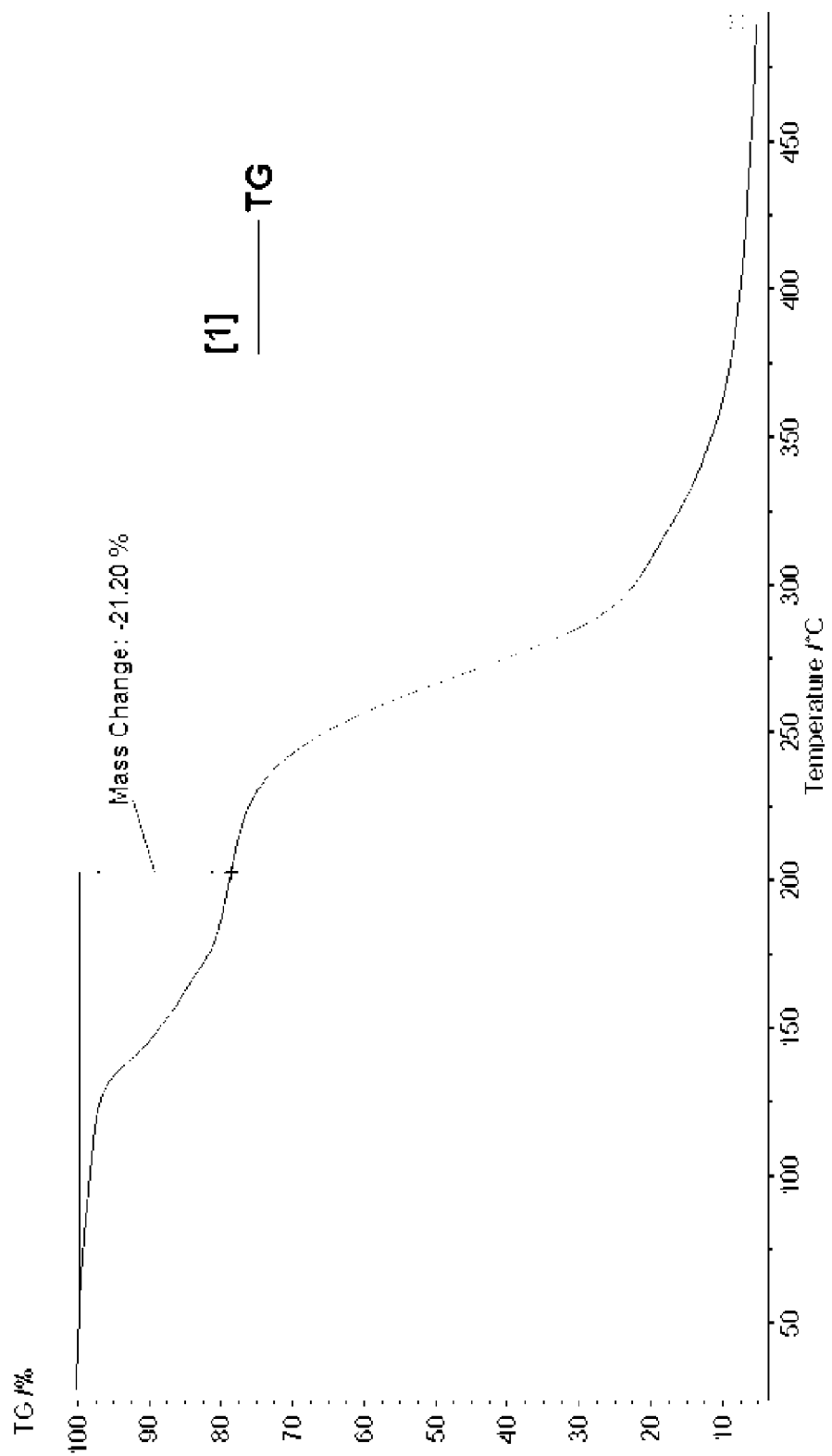

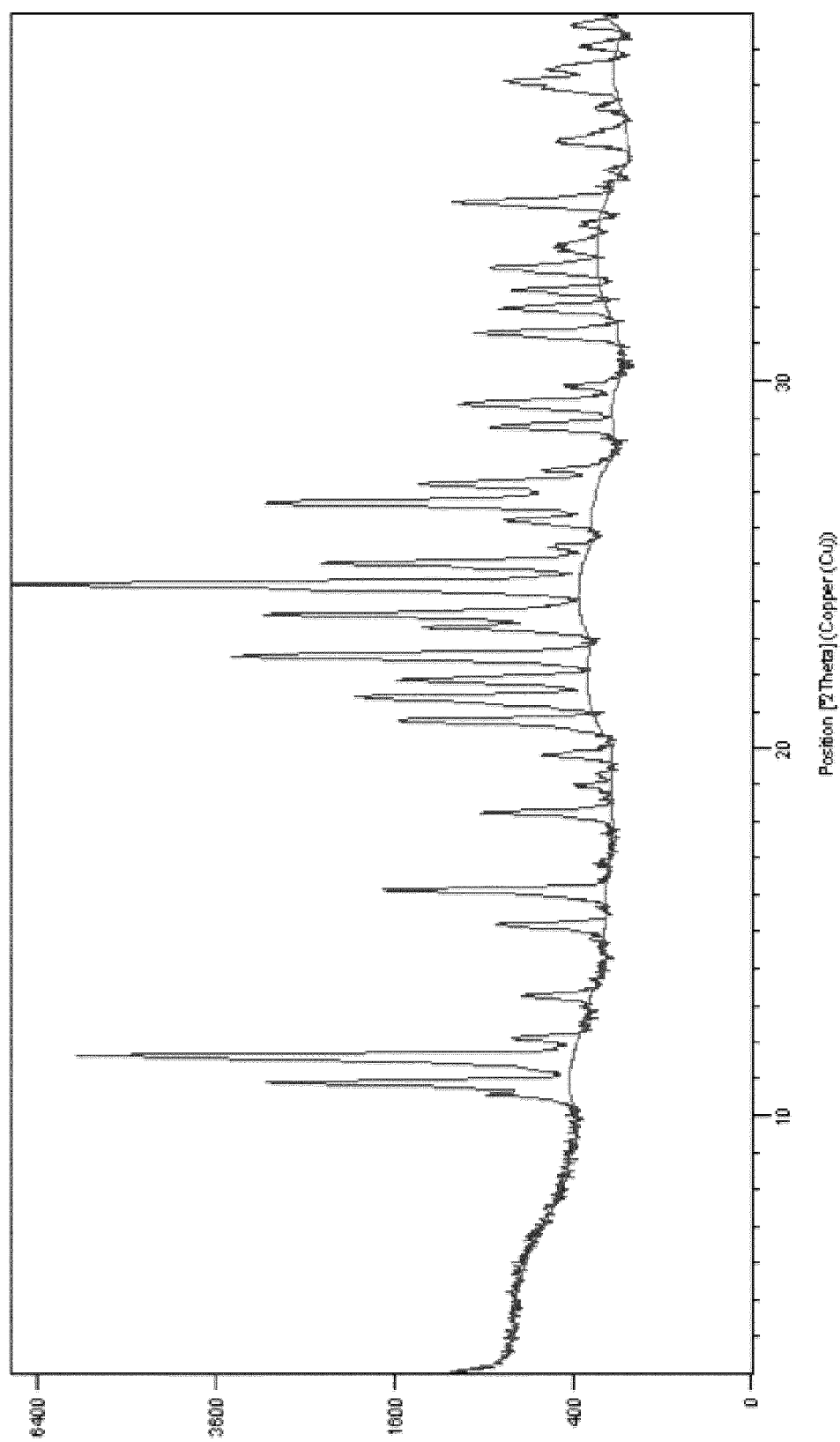
FIGURE 5 – PXRD of form II

FIGURE 6 – FTIR of form II
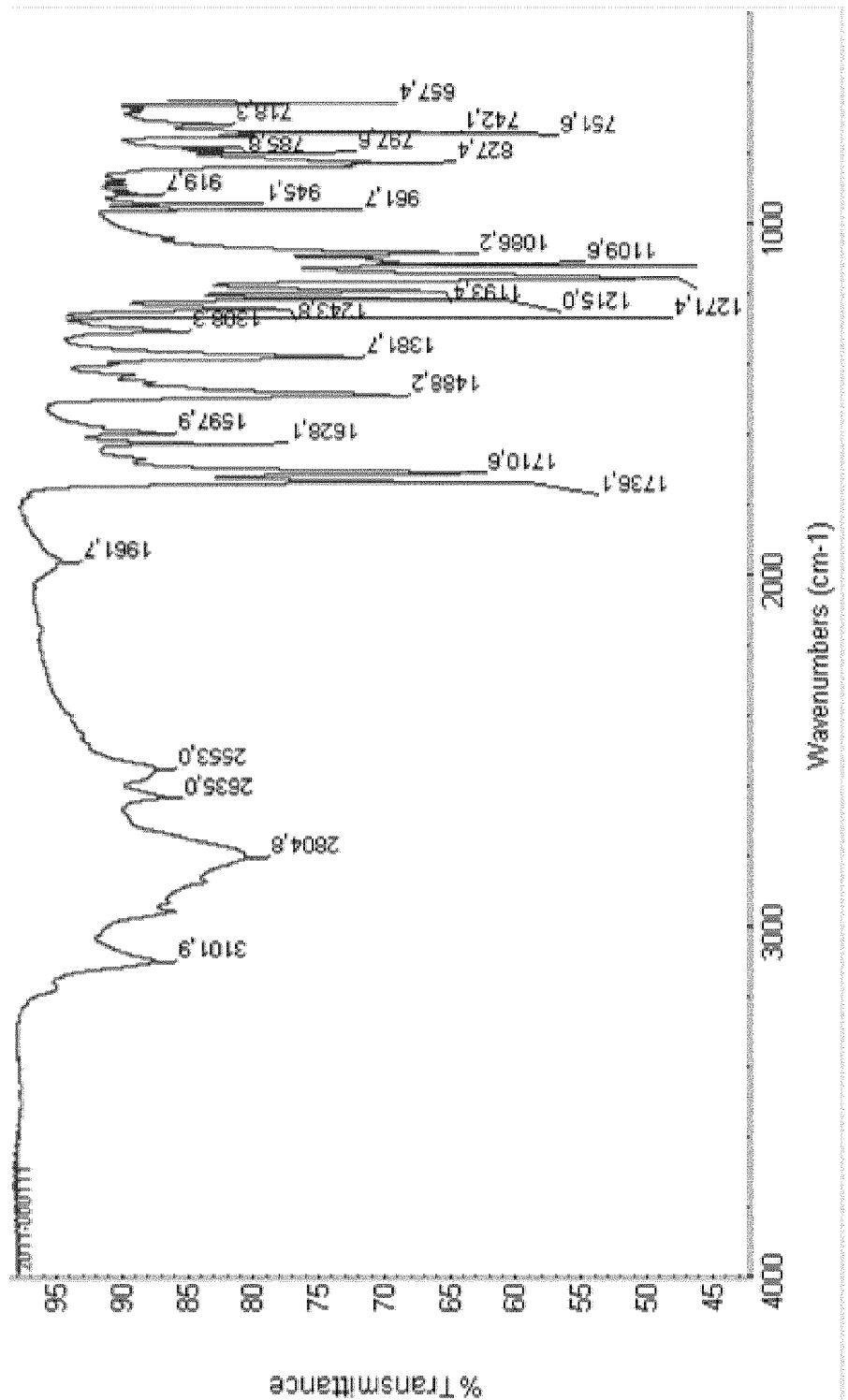

FIGURE 7 – DSC of form II
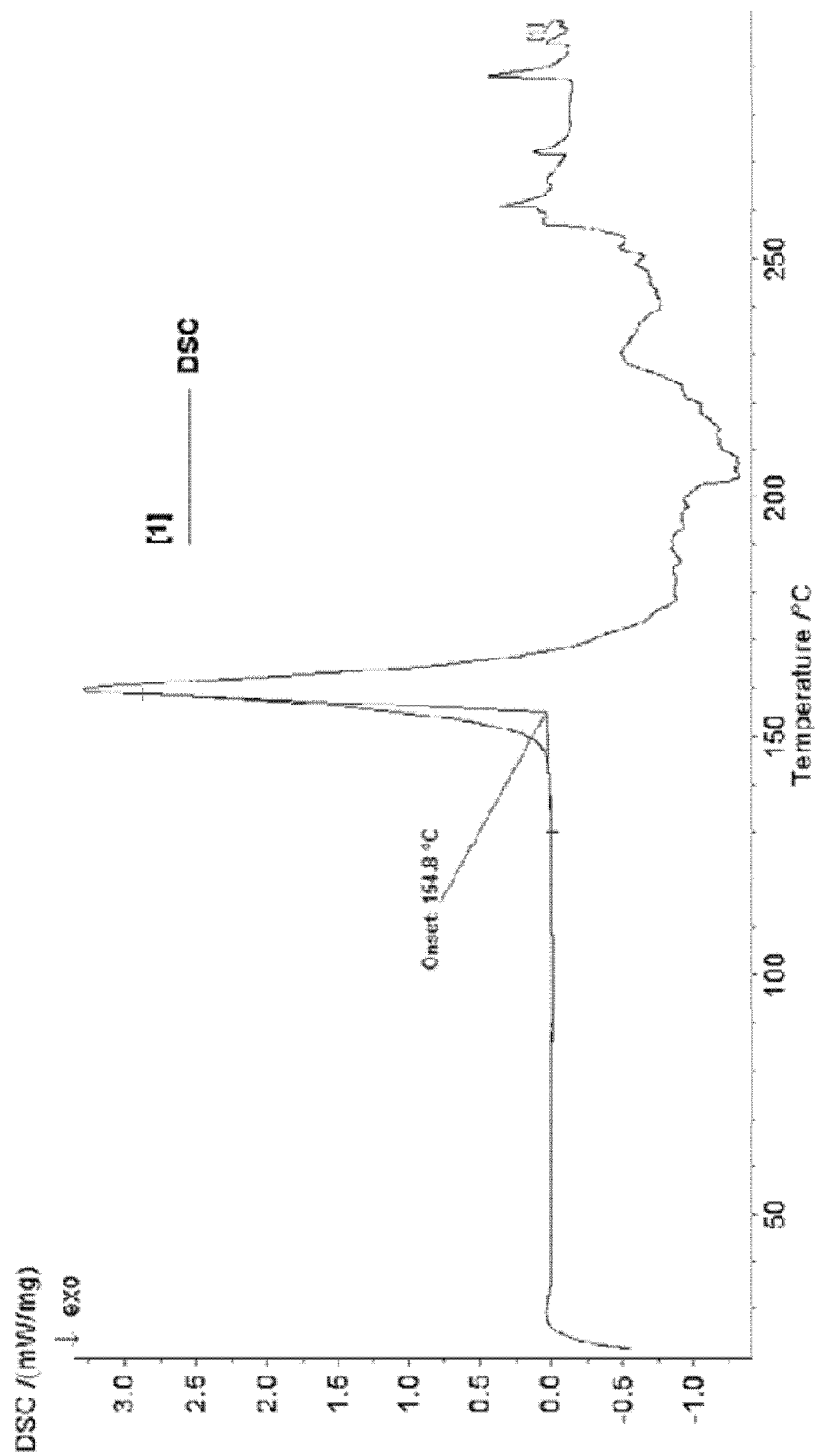

FIGURE 8 – TGA of form II
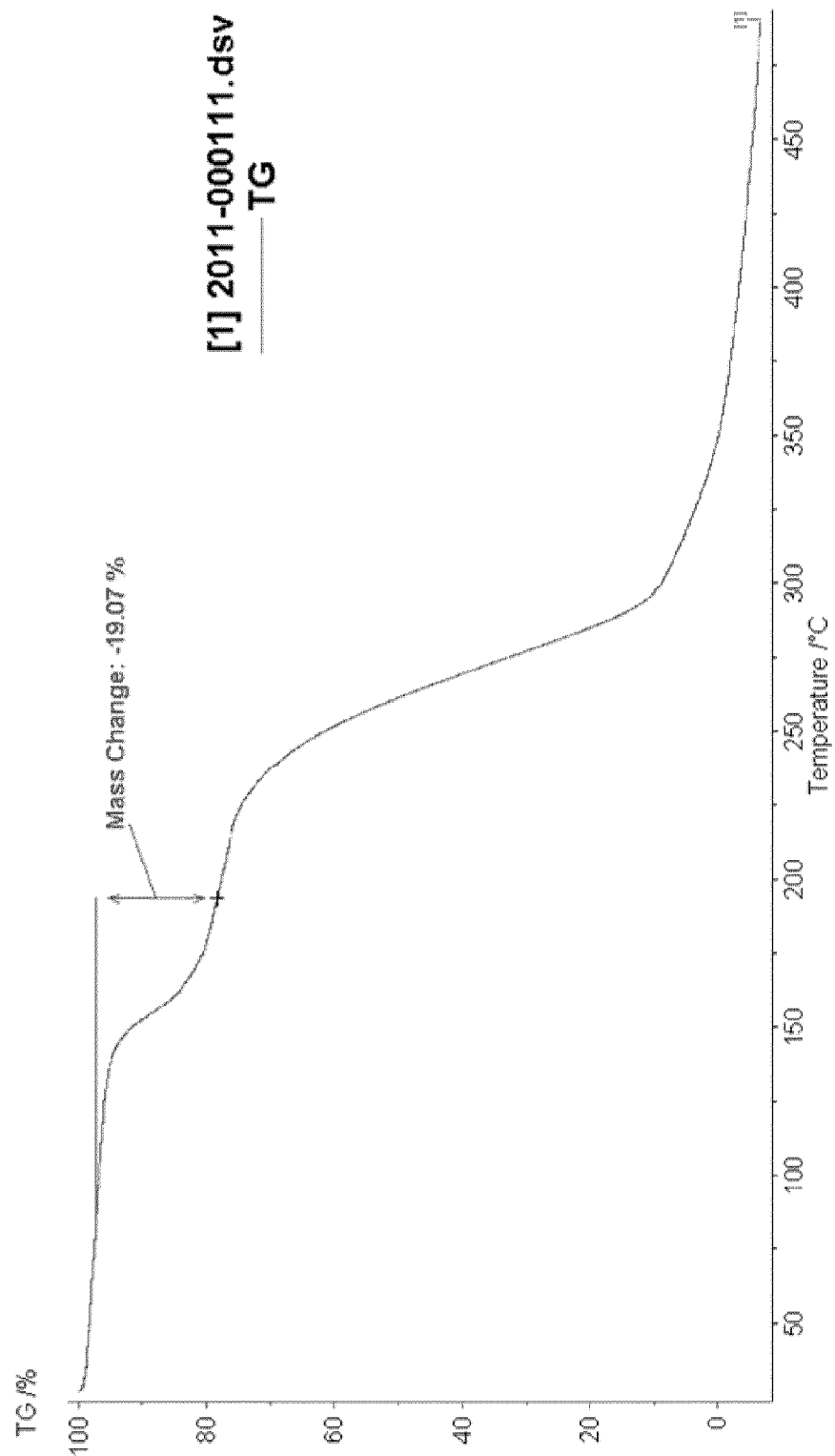

FIGURE 9 – PXRD of form III
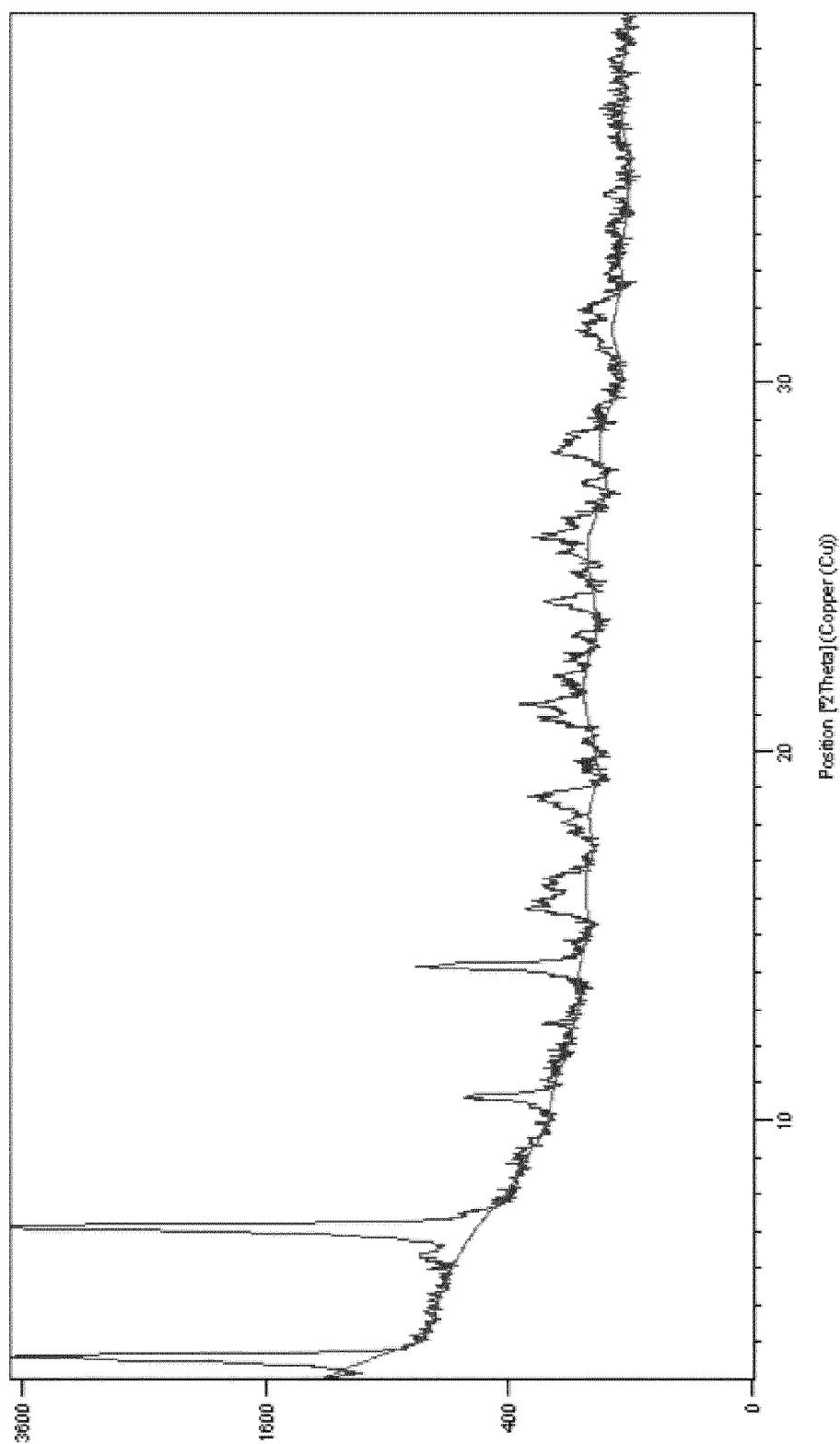

FIGURE 10 – FTIR of form III
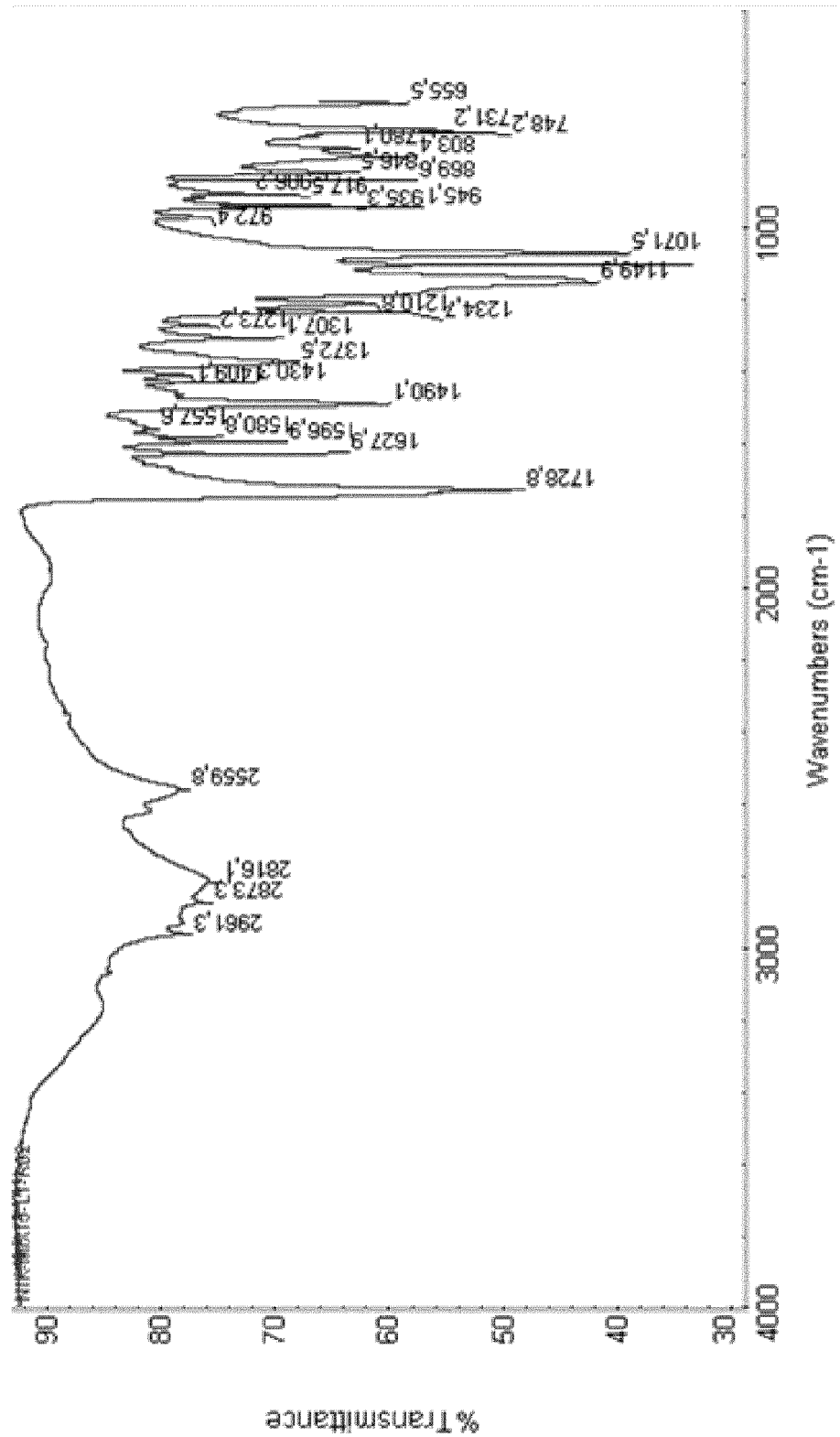

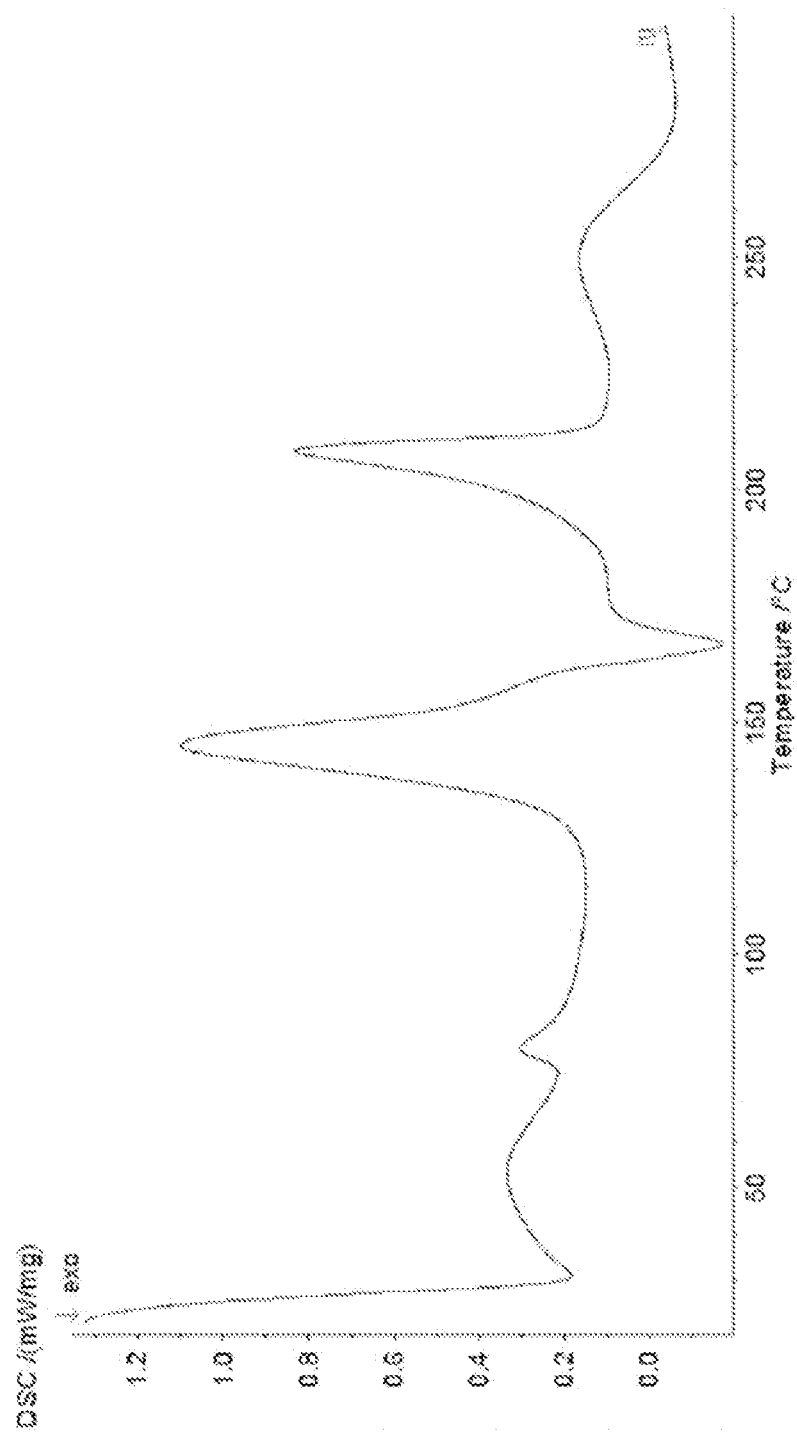
FIGURE 11 – DSC of form III

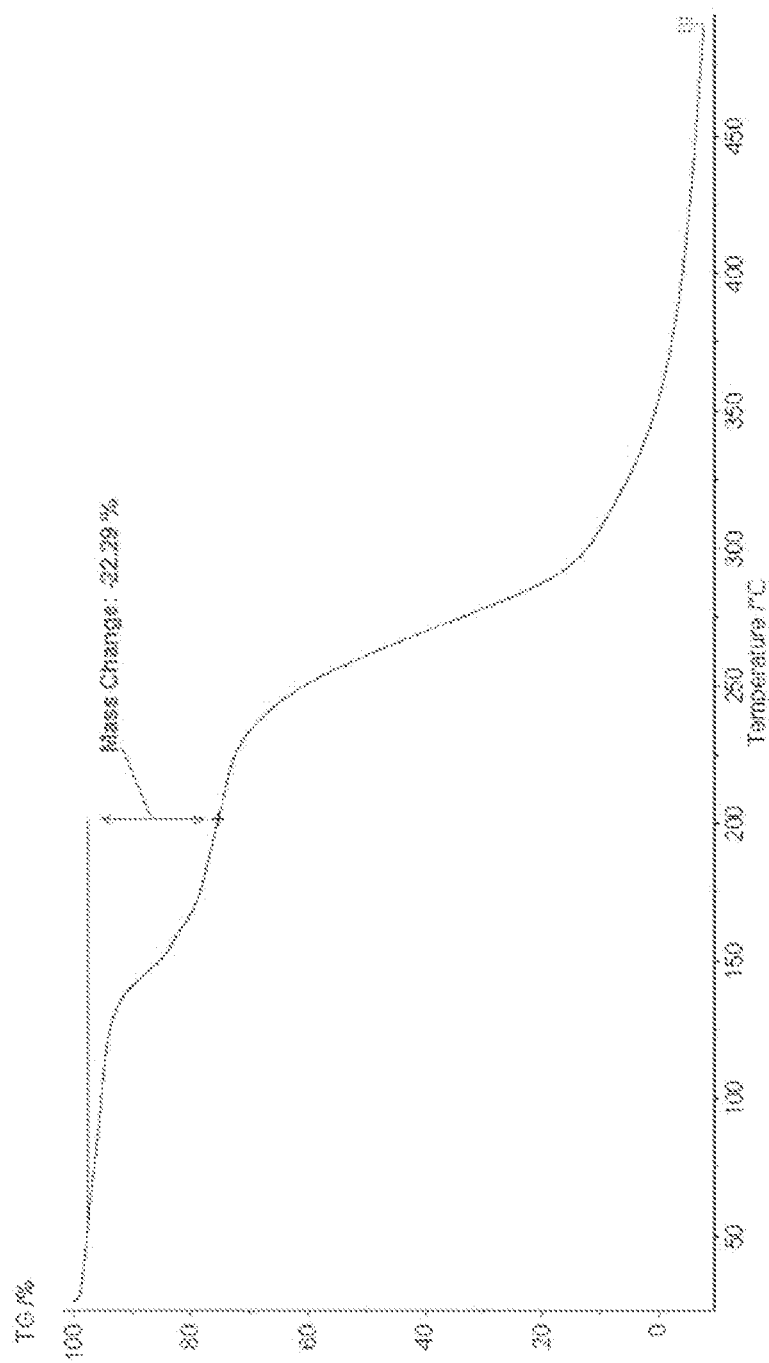

FIGURE 13 – PXRD of amorphous form
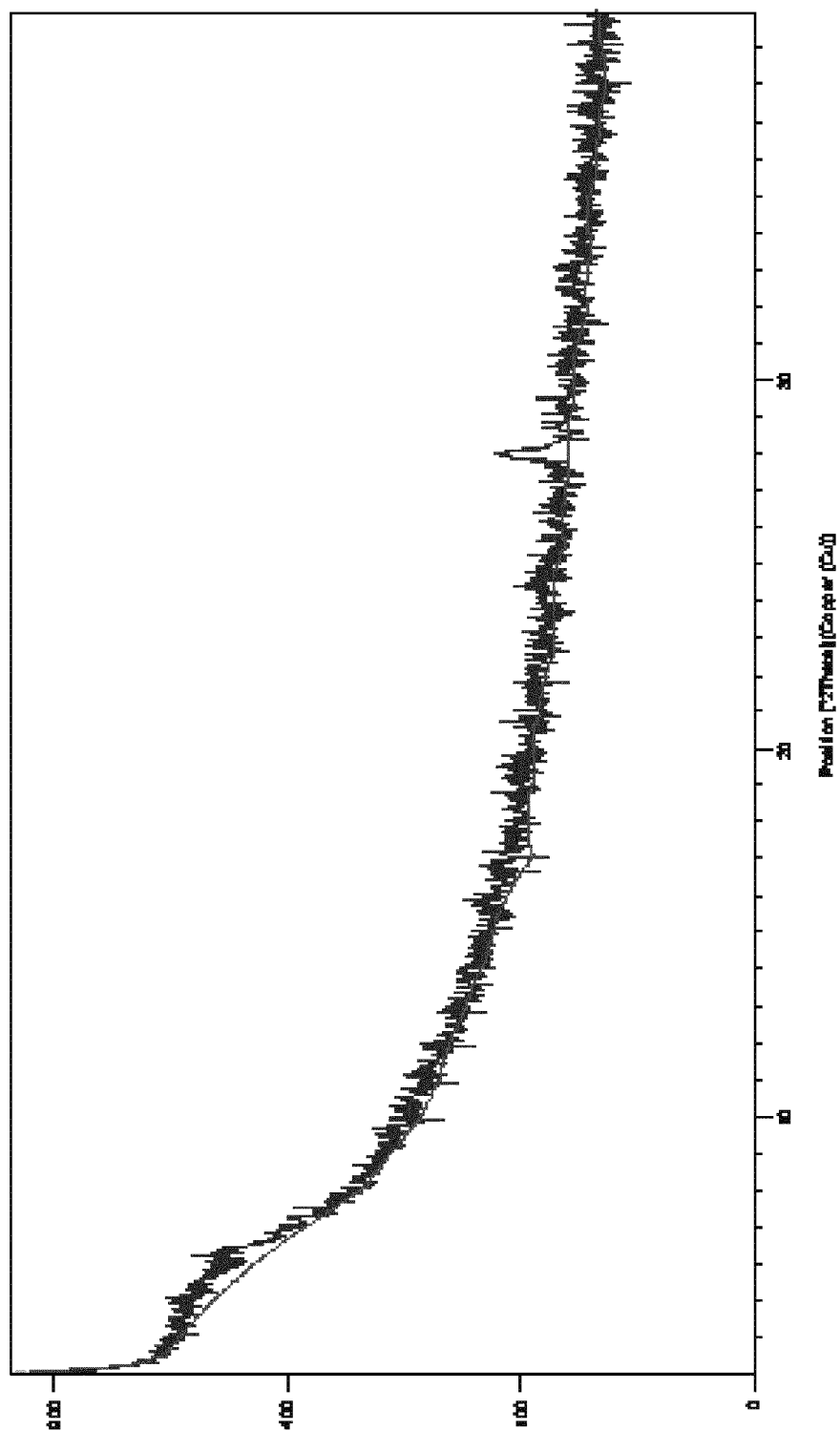

FIGURE 14 – FTIR of amorphous form
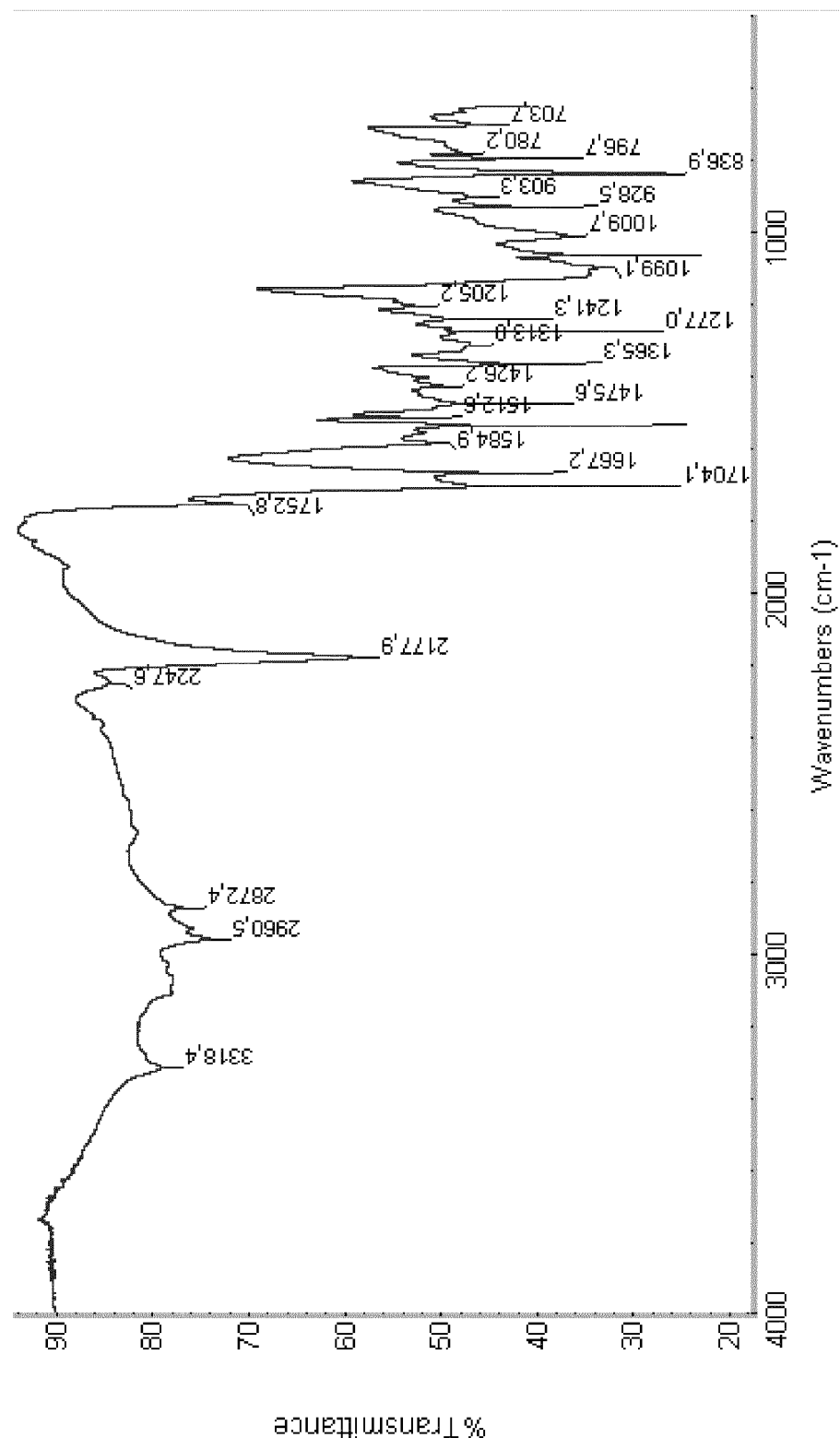

PRODRUG OF AN ANTI-INFLAMMATORY ACTIVE INGREDIENT

This application is a U.S. National Stage of PCT/EP2012/063414 filed Jul. 9, 2012, which claims priority to and the benefit of Italian Application No. MI2011A001288 filed Jul. 11, 2011, the contents of which applications are incorporated herein by reference in their entirety.

The present invention relates to a process for the preparation of a prodrug of 5-aminosalicylic acid, more particularly a process for the preparation of 2-butanoyloxy-5-amino-benzoic acid and solid forms of such compound.

The use of prodrugs of active ingredients is widespread in therapy. Prodrugs are derivatives of the active ingredient that show more favorable characteristics of bioavailability and once they reach their site of action they are metabolized into the active ingredient, exerting then an overall stronger pharmacological action than the active ingredient itself.

5-amino-salicylic acid or Mesalazine is a compound with anti-inflammatory activity widely used in the treatment of inflammatory diseases such as Crohn's disease and ulcerative colitis.

Among the possible prodrugs of such active ingredient those species wherein the phenolic group is esterified with carboxylic acids with medium chain, particularly with a butyryl group, are interesting.

The chemical structure of the butyric derivative, and more precisely of 2-butanoyloxy-5-amino-benzoic acid is represented by the following formula:

(I)

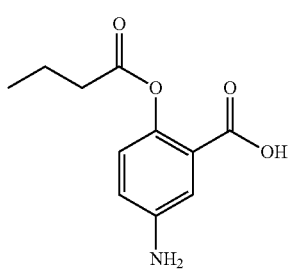

Derivatives of 5-aminosalicylic acid bearing an acyl on the phenolic group are known in literature and are generally prepared starting from 5-aminosalicylic acid by protection of the amino group, acylation of the phenolic group and subsequent amino deprotection. Such procedure becomes necessary because the direct acylation of 5-aminosalicylic acid leads to a double acylation of the substrate both on the amino and the phenolic group. By controlled deacylation, the N-monoacyl derivative but not the O-monoacyl derivative can be obtained.

For example, WO2004000786 describes the preparation of the propanoyloxy derivative of 5-aminosalicylic acid through the following synthetic scheme:

Scheme 1

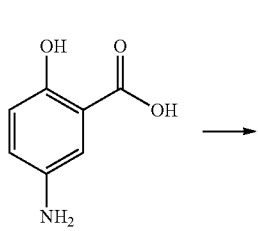

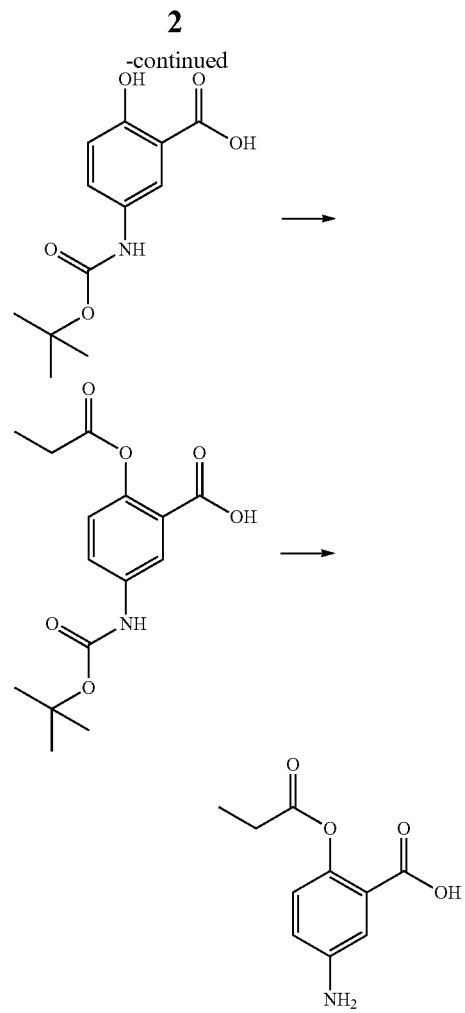

This method of synthesis results to be difficult and not particularly attractive from an industrial point of view.

We have now found that 2-butanoyloxy-5-amino-benzoic acid can be advantageously prepared through a process that avoids the problem of the protection and of the subsequent deprotection of the reactive functions of the molecule with the consequent reduction of the number of synthetic steps.

It is therefore object of the present invention a process for the synthesis of 2-butanoyloxy-5-amino-benzoic acid comprising the following steps:
a) the acylation of 5-nitrosalicylic acid by reaction with a butyric acid reactive derivative, optionally in the presence of an acid catalyst;
b) the reduction of the nitro group;
c) the optional crystallization of the resultant product.

The synthetic process object of the present invention is reported in the following scheme:

Scheme 2

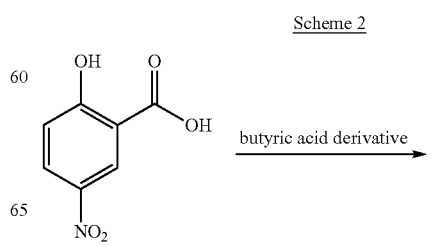

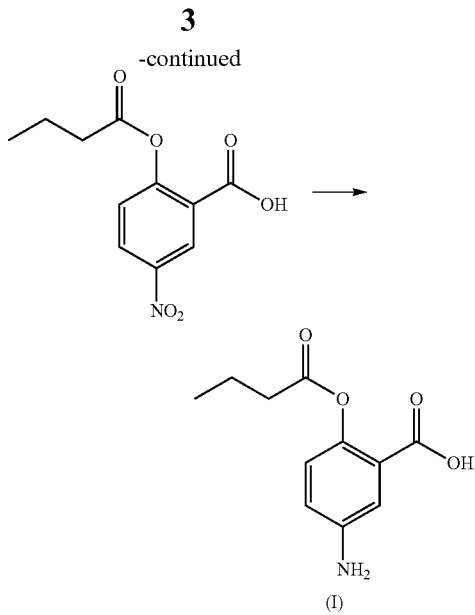

The first synthetic step of the process object of the present invention is carried out starting from 5-nitrosalicylic acid by reaction with a butyric acid reactive derivative, such as butyric anhydride or a butyryl halide, for example butyryl chloride or bromide.

Butyric anhydride is preferably used.

The reaction can be optionally carried out in the presence of an acid catalyst, such as for example methanesulfonic acid, p.toluenesulfonic acid, sulfuric acid or hydrogen halides.

Methanesulfonic acid is preferably used.

The acylation is carried out in a suitable organic solvent such as, for example, acetonitrile, dichloromethane or ethyl acetate.

The resultant 2-butanoyloxy-5-nitro-benzoic acid is reduced with conventional techniques obtaining the corresponding 5-amino derivative, preferably as a salt.

The reduction reaction of the nitro group is preferably carried out by catalytic hydrogenation in the presence of an inorganic acid.

The hydrogenation in the presence of catalytic amounts of Pd in a solution of hydrochloric acid in an organic solvent, for example dioxane, is particularly preferred.

To increase the purity of the resultant 2-butanoyloxy-5-amino-benzoic acid hydrochloride the crystallization of the product in a suitable solvent can be necessary.

We have found that 2-butanoyloxy-5-amino-benzoic acid hydrochloride can crystallize in different polymorphic forms.

Three crystalline forms of 2-butanoyloxy-5-amino-benzoic acid hydrochloride, named form I, form II and form III and an amorphous form were altogether characterized.

Such forms were characterized using PXRD (Powder X-Rays Diffraction), FTIR (Fourier Transform Infra Red), DSC (Differential Scanning Calorimetry) and TGA (Thermo Gravimetric Analysis) techniques.

The characterization of the crystalline forms I, II and III and of the amorphous form of 2-butanoyloxy-5-amino-benzoic acid hydrochloride was carried out using the following spectroscopic techniques, under the experimental conditions reported below:

PXRD (Powder X Ray Diffraction)
Experimental Conditions
Type of instrument: X'Pert PRO PANalytical
Type of measurement: Single scan
Wave lengths of measurement: Cu Kα1
Material constituting the anode: Cu
Voltage of the X-ray tube: 40
Power of the X-ray tube (mA): 40
Type of movement of the sample: Rotation
Rotation time of the sample (s): 1.0
Thickness of the filter (mm): 0.020
Filter material: Ni
Detector's name: X'Celerator
Type of detector: RTMS detector
Scan axis: Gonio
Scan range (°): 3.0000-39.9987
Width of the measurement range (°): 0.0167
Number of points: 2214
Scan mode: Continuous
Counting time (s): 12.700
Application software: X'Pert Data Collector vs. 2.2d
Control software of the instrument: XPERT-PRO vs. 1.9B
Temperature Room temperature
FT-IR (ATR)
Experimental Conditions
Type of instrument: Nicolet FT-IR 6700 ThermoFischer
Spectral range (Standard): 7800-350 $cm^{-1}$
Spectral range (Option, Csl Optics): 6400-200 $cm^{-1}$
Spectral range (Option, Extended-Range Optics): 11000-375 $cm^{-1}$
Spectral range (Option, Multi-Range Optics): 27000-15 $cm^{-1}$
Optical resolution: 0.09 $cm^{-1}$
Background noise peak to peak (1 min. scan): <8.68×10−6 AU*
Background noise RMS (1 minute scan): <1.95×10−6 AU*
Ordinate linearity: 0.07% T
Wavelength precision: 0.01 $cm^{-1}$
Minimum linear scan speed: 0.158 cm/sec
Maximum linear scan speed: 6.33 cm/sec
Number of scan speed: 15
Rapid scan (Spectra/second @16 $cm^{-1}$, 32 $cm^{-1}$): 65, 95
Number of scans of the sample: 32
Number of background scans: 32
Resolution: 4.000 $cm^{-1}$
Gain of the sample: 8.0
Optical speed: 0.6329
Opening: 100,00
Detector: DTGS KBr
Beam splitter: KBr
Source: IR
DSC
Experimental Conditions
Type of instrument: Perkin Elmer DSC-7
Calorimetric precision better than ±0.1%
Temperature precision ±0.1%
Temperature accuracy ±0.1%
Heating rate 10° C./min
Heating ramp from 30° C. to 250° C.
Sample preparation 1 mg in a 50µ perforated capsule
Thermal controller TAC 7/ΔX
TGA
Experimental Conditions
Type of instrument: STA 409 PC Luxx® Netzsch
Heating and cooling rate: 0.01 K/min . . . 50 K/min
TG resolution: up to 0.00002%
DSC resolution: <1 µW (K sensor)
DSC sensibilità: 8 µV/mW (K sensor)
Atmosphere: Inert (Nitrogen)
Gas flow control: 2 purge gases and 1 protective gas Purge gas: Nitrogen
Purge gas speed: 60 ml/min
Protective gas: Nitrogen
Protective gas speed: 20 ml/min
Crucible: DSC/TG pan Al
Heating rate: 10° C./min
DSC Heating ramp: from 30° C. to 280° C.
TGA Heating ramp: from 40° C. to 500° C.

SHORT DESCRIPTION OF THE FIGURES

FIG. 1—PXRD of form I
FIG. 2—FTIR of form I
FIG. 3—DSC of form I
FIG. 4—TGA of form I
FIG. 5—PXRD of form II
FIG. 6—FTIR of form II
FIG. 7—DSC of form II
FIG. 8—TGA of form II
FIG. 9—PXRD of form III
FIG. 10—FTIR of form III
FIG. 11—DSC of form III
FIG. 12—TGA of form III
FIG. 13—PXRD of amorphous form
FIG. 14—FTIR of amorphous form The crystalline form I of 2-butanoyloxy-5-amino-benzoic acid hydrochloride is an object of the present invention.

Form I according to the present invention has a PXRD with peaks at 4.7; 8.2; 9.5; 11.0; 11.7; 14.2; 16.5; 17.1; 20.7; 22.6; 24.5; 25.0; 29.0±0.20 2theta.

The form I of 2-butanoyloxy-5-amino-benzoic acid hydrochloride was characterized by PXRD, FTIR, DSC and TGA.

PXRD - Positions and characteristics of the relevant peaks
(uncertainty range on the position of the peak ±0.20 2theta)

| Pos. [°2Th.] | Height [cts] | FWHM [°2Th.] | d-spacing [Å] | Rel. Int. [%] |
|---|---|---|---|---|
| 4.7494 | 3291.60 | 0.1171 | 18.60635 | 100.00 |
| 4.8826 | 2163.52 | 0.0669 | 18.09875 | 65.73 |
| 8.2085 | 570.39 | 0.1338 | 10.77151 | 17.33 |
| 9.4608 | 908.98 | 0.1338 | 9.34839 | 27.62 |
| 11.0346 | 234.62 | 0.1004 | 8.01839 | 7.13 |
| 11.7385 | 227.28 | 0.0669 | 7.53911 | 6.90 |
| 12.5274 | 87.79 | 0.1673 | 7.06603 | 2.67 |
| 14.2111 | 868.58 | 0.1506 | 6.23242 | 26.39 |
| 14.3169 | 560.63 | 0.0502 | 6.18661 | 17.03 |
| 15.3247 | 41.64 | 0.2342 | 5.78197 | 1.27 |
| 16.5077 | 204.19 | 0.2007 | 5.37017 | 6.20 |
| 17.0983 | 644.99 | 0.1673 | 5.18597 | 19.59 |
| 17.5040 | 80.39 | 0.1004 | 5.06668 | 2.44 |
| 18.1659 | 110.38 | 0.2342 | 4.88355 | 3.35 |
| 19.9127 | 44.85 | 0.1673 | 4.45891 | 1.36 |
| 20.6708 | 555.17 | 0.1004 | 4.29707 | 16.87 |
| 20.7770 | 410.19 | 0.0669 | 4.27535 | 12.46 |
| 21.5054 | 99.35 | 0.1338 | 4.13216 | 3.02 |
| 22.0251 | 136.41 | 0.1004 | 4.03581 | 4.14 |
| 22.6358 | 548.70 | 0.1673 | 3.92829 | 16.67 |
| 23.0698 | 140.21 | 0.1004 | 3.85536 | 4.26 |
| 23.7256 | 135.09 | 0.1171 | 3.75027 | 4.10 |
| 24.0648 | 78.58 | 0.1004 | 3.69817 | 2.39 |
| 24.5497 | 376.85 | 0.2007 | 3.62620 | 11.45 |
| 24.9596 | 647.66 | 0.0669 | 3.56758 | 19.68 |
| 26.3623 | 190.55 | 0.1171 | 3.38084 | 5.79 |
| 26.7412 | 123.54 | 0.1004 | 3.33379 | 3.75 |
| 27.3096 | 38.94 | 0.1338 | 3.26569 | 1.18 |
| 27.6395 | 86.08 | 0.1338 | 3.22746 | 2.62 |
| 28.0423 | 21.29 | 0.1338 | 3.18200 | 0.65 |
| 28.4646 | 264.37 | 0.1338 | 3.13575 | 8.03 |
| 29.0116 | 453.88 | 0.1506 | 3.07786 | 13.79 |
| 29.7970 | 153.73 | 0.1673 | 2.99850 | 4.67 |
| 31.5868 | 71.04 | 0.2342 | 2.83257 | 2.16 |
| 32.3257 | 201.69 | 0.1338 | 2.76948 | 6.13 |
| 33.1705 | 88.95 | 0.1338 | 2.70086 | 2.70 |
| 33.4710 | 130.88 | 0.1673 | 2.67729 | 3.98 |
| 34.4577 | 153.06 | 0.1020 | 2.60070 | 4.65 |
| 34.5804 | 153.82 | 0.0836 | 2.59390 | 4.67 |
| 34.9696 | 57.45 | 0.2007 | 2.56591 | 1.75 |
| 35.4372 | 35.39 | 0.1338 | 2.53313 | 1.08 |
| 36.3873 | 112.55 | 0.2007 | 2.46914 | 3.42 |
| 37.0786 | 27.91 | 0.1338 | 2.42467 | 0.85 |
| 37.4940 | 37.63 | 0.1673 | 2.39876 | 1.14 |
| 38.0974 | 133.58 | 0.2007 | 2.36214 | 4.06 |
| 39.3147 | 57.63 | 0.1004 | 2.29177 | 1.75 |

The profile of the diffractogram of form I is reported in FIG. 1.

FTIR—the FTIR profile of form I is reported in FIG. 2.

DSC—the profile related to form I is reported in FIG. 3. It shows an onset at 142.5° C.

TGA—the TGA profile related to form I is reported in FIG. 4.

The form I of 2-butanoyloxy-5-amino-benzoic acid hydrochloride can be prepared by crystallization of 2-butanoyloxy-5-amino-benzoic acid hydrochloride from toluene and acetone. The crystallization is preferably carried out by dissolving 2-butanoyloxy-5-amino-benzoic acid hydrochloride in toluene at a temperature between room temperature and 70° C., preferably between 30° C. and 50° C., and then by adding acetone. By cooling of the solution, preferably at room temperature a suspension is formed from which the crystalline form I is isolated by filtration, washing and drying.

Crystalline form II of 2-butanoyloxy-5-amino-benzoic acid hydrochloride is an object of the present invention.

Form II according to the present invention has a PXRD with peaks at 10.9; 11.6; 15.2; 16.1; 18.2; 20.8; 21.4; 21.9; 22.5; 23.3; 23.7; 24.5; 25.0; 26.7; 27.2±0.20 2theta.

The form II of 2-butanoyloxy-5-amino-benzoic acid hydrochloride was characterized by PXRD, FTIR, DSC and TGA.

PXRD - Positions and characteristics of the relevant peaks
(uncertainty range on the position of the peak ±0.20 2theta)

| Pos. [°2Th.] | Height [cts] | FWHM [°2Th.] | d-spacing [Å] | Rel. Int. [%] |
|---|---|---|---|---|
| 10.5768 | 475.72 | 0.0669 | 8.36441 | 7.31 |
| 10.9220 | 2476.66 | 0.1171 | 8.10080 | 38.03 |
| 11.6337 | 5247.96 | 0.1004 | 7.60677 | 80.59 |
| 12.1300 | 358.24 | 0.0836 | 7.29664 | 5.50 |
| 13.2907 | 318.25 | 0.1171 | 6.66188 | 4.89 |
| 15.1965 | 551.37 | 0.1171 | 5.83045 | 8.47 |
| 16.1404 | 1429.54 | 0.1506 | 5.49154 | 21.95 |
| 16.8495 | 30.39 | 0.2007 | 5.26199 | 0.47 |
| 18.2465 | 647.88 | 0.1338 | 4.86215 | 9.95 |
| 18.9985 | 140.77 | 0.1004 | 4.67137 | 2.16 |
| 19.2829 | 51.36 | 0.1004 | 4.60310 | 0.79 |
| 19.8734 | 287.51 | 0.1338 | 4.46764 | 4.42 |
| 20.7663 | 1279.08 | 0.1338 | 4.27751 | 19.64 |
| 21.1909 | 508.15 | 0.0502 | 4.19275 | 7.80 |
| 21.4180 | 1603.79 | 0.1338 | 4.14882 | 24.63 |
| 21.8717 | 1265.18 | 0.1338 | 4.06377 | 19.43 |
| 22.5215 | 3056.67 | 0.1506 | 3.94797 | 46.94 |
| 23.2973 | 987.32 | 0.1506 | 3.81822 | 15.16 |
| 23.6507 | 2628.10 | 0.1338 | 3.76198 | 40.36 |
| 24.4767 | 6511.66 | 0.1673 | 3.63686 | 100.00 |
| 25.0432 | 1983.44 | 0.1673 | 3.55586 | 30.46 |
| 25.5100 | 163.32 | 0.1004 | 3.49184 | 2.51 |
| 26.2111 | 454.22 | 0.1506 | 3.40001 | 6.98 |

| PXRD - Positions and characteristics of the relevant peaks (uncertainty range on the position of the peak ±0.20 2theta) | | | | |
|---|---|---|---|---|
| Pos. [°2Th.] | Height [cts] | FWHM [°2Th.] | d-spacing [Å] | Rel. Int. [%] |
| 26.6562 | 2648.36 | 0.1673 | 3.34423 | 40.67 |
| 27.1982 | 1101.18 | 0.1673 | 3.27881 | 16.91 |
| 27.5733 | 273.93 | 0.0836 | 3.23506 | 4.21 |
| 28.7092 | 557.74 | 0.1338 | 3.10959 | 8.57 |
| 29.3891 | 794.68 | 0.1506 | 3.03918 | 12.20 |
| 29.8867 | 196.75 | 0.0836 | 2.98970 | 3.02 |
| 31.2908 | 736.24 | 0.1840 | 2.85868 | 11.31 |
| 31.9773 | 492.59 | 0.1673 | 2.79886 | 7.56 |
| 32.4540 | 430.54 | 0.1171 | 2.75883 | 6.61 |
| 33.0666 | 570.26 | 0.1673 | 2.70910 | 8.76 |
| 33.5393 | 146.62 | 0.1338 | 2.67200 | 2.25 |
| 33.7299 | 148.82 | 0.1338 | 2.65733 | 2.29 |
| 34.2216 | 68.59 | 0.1338 | 2.62027 | 1.05 |
| 34.8428 | 852.67 | 0.1673 | 2.57496 | 13.09 |
| 35.3379 | 13.31 | 0.1338 | 2.54001 | 0.20 |
| 35.6993 | 57.78 | 0.1338 | 2.51513 | 0.89 |
| 36.4753 | 269.57 | 0.2007 | 2.46338 | 4.14 |
| 37.3876 | 89.31 | 0.0502 | 2.40534 | 1.37 |
| 37.8926 | 250.71 | 0.1004 | 2.37444 | 3.85 |
| 38.1350 | 525.65 | 0.1004 | 2.35990 | 8.07 |
| 38.4503 | 286.00 | 0.0836 | 2.34127 | 4.39 |
| 39.1109 | 125.92 | 0.1338 | 2.30323 | 1.93 |
| 39.6235 | 168.51 | 0.1338 | 2.27461 | 2.59 |

The profile of the diffractogram of form II is reported in FIG. 5.

FTIR—the FTIR profile of form II is reported in FIG. 6.

DSC—the profile related to form II is reported in FIG. 7. It shows an onset at 154.8° C.

TGA—the TGA profile related to form II is reported in FIG. 8.

The form II of 2-butanoyloxy-5-amino-benzoic acid hydrochloride can be prepared by conversion of form I.

The preparation of form II is preferably carried out by suspending 2-butanoyloxy-5-amino-benzoic acid hydrochloride form I in an organic solvent selected among methyl-t-butyl ether, dimethoxyethane, diethylether, dioxane, isopropylether, anisole, dichloromethane, chloroform, ethyl formate, propylacetate, ethylacetate, methylacetate, diethyl carbonate, acetonitrile, benzonitrile, nitromethane, cyclopentanone, 3-pentanone and acetone at a temperature around room temperature and maintaining the suspension at such temperature for several hours. Form II is then obtained by filtration of the suspension.

Alternatively, the conversion of form I into form II can be carried out by maintaining form I under an atmosphere of controlled humidity for several hours at a temperature around room temperature.

The water content in the form II object of the present invention is about 0.4-0.5%.

Crystalline form III of 2-butanoyloxy-5-amino-benzoic acid hydrochloride is an object of the present invention.

Form III according to the present invention has a PXRD with peaks at 3.6; 7.1; 10.6; 14.2±0.20 2theta.

The form III of 2-butanoyloxy-5-amino-benzoic acid hydrochloride was characterized by PXRD, FTIR, DSC and TGA.

| PXRD - Positions and characteristics of the relevant peaks (uncertainty range on the position of the peak ±0.20 2theta) | | | | |
|---|---|---|---|---|
| Pos. [°2Th.] | Height [cts] | FWHM [°2Th.] | d-spacing [Å] | Rel. Int. [%] |
| 3.6347 | 2587.49 | 0.1338 | 24.30926 | 86.59 |
| 7.1396 | 2988.27 | 0.1673 | 12.38173 | 100.00 |
| 9.0279 | 30.10 | 0.4015 | 9.79566 | 1.01 |
| 10.6479 | 268.52 | 0.1673 | 8.30867 | 8.99 |
| 12.6230 | 59.07 | 0.2007 | 7.01272 | 1.98 |
| 14.1753 | 533.95 | 0.1840 | 6.24810 | 17.87 |
| 15.7155 | 144.52 | 0.1004 | 5.63905 | 4.84 |
| 16.5365 | 91.47 | 0.3346 | 5.36088 | 3.06 |
| 18.7841 | 120.21 | 0.4015 | 4.72419 | 4.02 |
| 19.6032 | 20.25 | 0.2676 | 4.52861 | 0.68 |
| 20.2273 | 13.91 | 0.2007 | 4.39026 | 0.47 |
| 20.8639 | 111.67 | 0.1673 | 4.25773 | 3.74 |
| 21.2880 | 174.67 | 0.1004 | 4.17386 | 5.85 |
| 22.0406 | 70.97 | 0.1673 | 4.03301 | 2.37 |
| 22.5229 | 38.96 | 0.2007 | 3.94773 | 1.30 |
| 23.1599 | 46.20 | 0.1338 | 3.84057 | 1.55 |
| 24.0391 | 112.21 | 0.1338 | 3.70207 | 3.76 |
| 24.8095 | 31.56 | 0.2007 | 3.58882 | 1.06 |
| 25.3720 | 69.40 | 0.1338 | 3.51051 | 2.32 |
| 25.7851 | 145.59 | 0.1338 | 3.45521 | 4.87 |
| 26.2812 | 60.79 | 0.2007 | 3.39110 | 2.03 |
| 27.2727 | 48.14 | 0.2007 | 3.27003 | 1.61 |
| 28.0575 | 107.41 | 0.1338 | 3.18031 | 3.59 |
| 28.6040 | 78.04 | 0.1004 | 3.12079 | 2.61 |
| 29.3231 | 24.12 | 0.3346 | 3.04588 | 0.81 |
| 31.3670 | 60.22 | 0.2676 | 2.85191 | 2.02 |
| 31.9768 | 62.35 | 0.2007 | 2.79890 | 2.09 |
| 34.2012 | 27.44 | 0.3346 | 2.62178 | 0.92 |
| 35.0471 | 42.99 | 0.1338 | 2.56042 | 1.44 |
| 38.7343 | 19.20 | 0.4015 | 2.32476 | 0.64 |

The profile of the diffractogram of form III is reported in FIG. 9.

FTIR—the FTIR profile of form III is reported in FIG. 10.

DSC—the profile related to form III is reported in FIG. 11. It does not show fusion peaks.

TGA—the TGA profile related to form III is reported in FIG. 12.

The form III of 2-butanoyloxy-5-amino-benzoic acid hydrochloride can be prepared by conversion of form I.

The preparation of form III is preferably carried out starting from 2-butanoyloxy-5-amino-benzoic acid hydrochloride form I by crystallization from a solvent selected among isopropanol, isobutanol and acetone. The crystallization is preferably carried out by dissolving form I in a solvent and leaving the solution evaporating at a temperature around room temperature up to obtain a crystalline solid.

The amorphous form of 2-butanoyloxy-5-amino-benzoic acid hydrochloride is an object of the present invention.

The amorphous form was characterized by PXRD and FTIR.

PXRD—the profile of the diffractogram does not show defined diffraction peaks as occurs for amorphous products.

The profile of the diffractogram of the amorphous form is reported in FIG. 13.

FTIR—the FTIR profile of the amorphous form is reported in FIG. 14.

In order to better illustrate the present invention, without however limiting it, the following examples are now given.

Example 1

Preparation of 2-butanoyloxy-5-nitro-benzoic acid 50 g of 5-nitrosalycilic acid, 50 ml of acetonitrile, 111.7 ml of butyric anhydride and 0.18 ml of methanesulfonic acid were loaded into a 500 ml reactor under nitrogen atmosphere. The mixture was heated under stirring to 80±2° C. up to obtain a complete dissolution. The mixture was maintained at 76±2° C. for 2 hours, then cooled to 25° C. in about two hours and kept under stirring for 16 hours. At the end the solvent was evaporated at 40° C. under vacuum and the residual was added with 70 ml of dichloromethane. 500 ml of heptane were then added in one hour to the resultant solution. A precipitate formed in suspension, that was kept under stirring at room temperature for one hour and for one hour at 0° C., for being then filtered on a buckner and washed with two aliquots of 70 ml of heptane. The solid was dried at 35° C. under vacuum (30 mmHg) for two hours giving 35 g of the expected product (51% yield).

Example 2

Preparation of crude 2-butanoyloxy-5-amino-benzoic acid hydrochloride 10 g of 2-butanoyloxy-5-nitro-benzoic acid, 8.5 ml of dioxane, 1.5 ml of HCl 4M solution in dioxane and 1.0 g of Pd/C at 5% were loaded into a 300 ml reactor at 16±2° C. After two vacuum-nitrogen cycles, the reactor was saturated with hydrogen at 10 bar and kept at 16±2° C. for 6 hours. At the end, nitrogen atmosphere was restored in the reactor and the reaction mixture was added with 125 ml of acetone at 25° C. The suspension was stirred at 25° C. for 30 minutes to obtain the dissolution of the undissolved product and the carbon suspension was filtered on a celite panel which was then washed with 60 ml of acetone. The resultant solution was then evaporated under vacuum at 30° C. and the solid residue was dried under vacuum at 35° C. for 4 hours to obtain 10 g of the expected product (99% yield).

Example 3

Preparation of 2-butanoyloxy-5-amino-benzoic acid hydrochloride crystalline form I 10 g of crude 2-butanoyloxy-5-amino-benzoic acid hydrochloride and 40 ml of toluene were loaded into a 250 ml reactor. The suspension was heated up to 40° C. and 90 ml of acetone were added at such temperature obtaining a solution. 25 ml of toluene were then added to the mixture obtaining a slightly cloudy of the mixture. The mixture was cooled to 25±2° C. in two hours and subsequently at 0±2° C. in 30 minutes, and kept at such temperature for one hour. The resultant suspension was filtered on a buckner and washed with two aliquots of 15 ml of toluene. The wet solid was dried under vacuum at 35° C. for 6 hours, obtaining 5.5 g of 2-butanoyloxy-5-amino-benzoic acid hydrochloride crystalline form I.

Example 4

Preparation of 2-butanoyloxy-5-amino-benzoic acid hydrochloride crystalline form II 50 mg of 2-butanoyloxy-5-amino-benzoic acid hydrochloride crystalline form I, prepared as described in example 3, were suspended in 2 ml of isopropyl acetate and kept under such conditions at room temperature for 7 days. At the end the product was filtered and analyzed. PXRD showed that the crystalline form of the resultant product was the form II.

Example 5

Preparation of 2-butanoyloxy-5-amino-benzoic acid hydrochloride crystalline form II By working in a similar manner as described in example 4, but using as dispersing medium, for each experiment, one of the following solvents: methyl-t-butyl ether, dimethoxyethane, diethylether, dioxane, isopropylether, anisole, dichloromethane, chloroform, ethyl formate, propylacetate, ethylacetate, methylacetate, diethylcarbonate, acetonitrile, benzonitrile, nitromethane, cyclopentanone, 3-pentanone and acetone, a crystalline solid which resulted to be the form II was obtained.

Example 6

Preparation of 2-butanoyloxy-5-amino-benzoic acid hydrochloride crystalline form II 1.0 g of 2-butanoyloxy-5-amino-benzoic acid hydrochloride crystalline form I, prepared as described in example 3, were introduced in a laboratory dryer in which lower portion a saturated $K_2CO_3$ solution was prepared. The temperature was kept constant at 20° C. to obtain a relative humidity of about 43% inside the dryer. After 24 hours a sample was removed and the crystalline form was analyzed by X ray. PXRD showed that the crystalline form of the resultant product was the form II. The water content of the sample increased from an initial value of 0.3% up to a final value of 0.42%.

Example 7

Preparation of 2-butanoyloxy-5-amino-benzoic acid hydrochloride crystalline form II 1.0 g of 2-butanoyloxy-5-amino-benzoic acid hydrochloride crystalline form I, prepared as described in example 3, were introduced in a laboratory dryer in which lower portion a saturated NaCl solution was prepared. The temperature was kept constant at 20° C. to obtain a relative humidity of about 75% inside the dryer. After 24 hours a sample was removed and the crystalline form was analyzed by X ray. PXRD showed that the crystalline form of the resultant product was the form II. The water content of the sample increased from an initial value of 0.3% up to a final value of 0.49%.

Example 8

Preparation of 2-butanoyloxy-5-amino-benzoic acid hydrochloride crystalline form III 50 mg of 2-butanoyloxy-5-amino-benzoic acid hydrochloride crystalline form I, prepared as described in example 3, were dissolved in 4 ml of isopropanol, filtered on a 0.45μ Whatman filter and the resultant solution was left to spontaneously evaporate at 4° C. for 7 days. The resultant solid was then analyzed. PXRD showed that the crystalline form of the resultant product was the form III.

Example 9

Preparation of 2-butanoyloxy-5-amino-benzoic acid hydrochloride crystalline form III By working in a similar manner as described in example 8 but using as solvent medium, for each experiment, a solvent selected among acetone and isobutanol, a crystalline solid was obtained which resulted to be the form III.

Example 10

Preparation of 2-butanoyloxy-5-amino-benzoic acid hydrochloride amorphous form 50 mg of 2-butanoyloxy-5-amino-benzoic acid hydrochloride crystalline form I, prepared as described in example 3, were dissolved in 4 ml of dichloromethane, filtered on a 0.45μ Whatman filter and the resultant solution was left to spontaneously evaporate at room temperature (25° C.) for 3 days. The resultant solid was then analyzed. PXRD showed that the crystalline form of the resultant product was amorphous.

The invention claimed is:

1. Crystalline Form I of 2-butanoyloxy-5-amino-benzoic acid hydrochloride characterized by a PXRD with peaks at 4.7; 8.2; 9.5; 11.0; 11.7; 14.2; 16.5; 17.1; 20.7; 22.6; 24.5; 25.0; 29.0±0.20 2theta.

* * * * *